United States Patent
Dose et al.

(10) Patent No.: US 9,885,032 B2
(45) Date of Patent: Feb. 6, 2018

(54) MULTISORT CELL SEPARATION METHOD

(71) Applicant: Miltenyi Biotec GmbH, Bergisch Gladbach (DE)

(72) Inventors: Christian Dose, Kurten (DE); Volker Huppert, Kürten (DE); Burgund Kauling, Bergisch Gladbach (DE); Philipp Steinbrück, Solingen (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 69 days.

(21) Appl. No.: 14/944,991

(22) Filed: Nov. 18, 2015

(65) Prior Publication Data

US 2016/0186165 A1 Jun. 30, 2016

(30) Foreign Application Priority Data

Dec. 27, 2014 (EP) .................... 14200362

(51) Int. Cl.
| | |
|---|---|
| *C12N 13/00* | (2006.01) |
| *B03C 1/01* | (2006.01) |
| *B03C 1/28* | (2006.01) |
| *C12N 5/00* | (2006.01) |
| *G01N 1/40* | (2006.01) |
| *G01N 33/543* | (2006.01) |

(52) U.S. Cl.
CPC ............. *C12N 13/00* (2013.01); *B03C 1/01* (2013.01); *B03C 1/288* (2013.01); *C12N 5/0087* (2013.01); *G01N 1/40* (2013.01); *G01N 33/54333* (2013.01); *B03C 2201/26* (2013.01); *G01N 2001/4038* (2013.01)

(58) Field of Classification Search
CPC ..... G01N 33/54333; G01N 2001/4038; G01N 1/40; B03C 2201/26; B03C 1/01; B03C 1/288; C12N 13/00; C12N 5/0087
See application file for complete search history.

(56) References Cited

FOREIGN PATENT DOCUMENTS

| | | | | |
|---|---|---|---|---|
| EP | 2597153 B1 | * 10/2016 | ............. | B01D 21/00 |
| WO | WO 9631776 A1 | * 10/1996 | ............. | B03C 1/002 |
| WO | WO 2013076070 A1 | * 5/2013 | ............. | B01D 21/00 |

OTHER PUBLICATIONS

Pierzchalski A. et al., "An Innovative Cascade System for Simultaneous Separation of Multiple Cell Types", PLOS ONE, Sep. 6, 2013, vol. 8, No. 9, e74745, pp. 1-9.*

* cited by examiner

*Primary Examiner* — Satyendra K Singh
(74) *Attorney, Agent, or Firm* — Jaquelin K. Spong

(57) ABSTRACT

The invention is directed to a method for enriching target cells from a sample of cells characterized by:

a) contacting the sample with a cell aggregation agent and first magnetic particles having an iron content of 0.1 pg to 5000 pg, coupled to a first antigen recognizing moiety; and second magnetic particles having an iron content of 0.05 fg to 100 fg and coupled to a second antigen recognizing moiety to obtain mixture a)

b) applying a first magnetic field gradient to the mixture a) thereby removing the cells bound to the first antigen recognizing moiety coupled to the first magnetic particles, to obtain a mixture b) and obtaining an agglomerate comprising the cells of mixture a) bound to the cell aggregation agent c) applying a second magnetic field gradient to the mixture b) thereby immobilizing the cells bound to the second antigen recognizing moiety d) recovering the immobilized cells from the second magnetic field gradient as target cells.

11 Claims, 6 Drawing Sheets ial fragments like F(ab), F(ab)2 or other fragments including recombinant fragments and bispecific antibodies, characterized in that they comprise at least two antigen-recognition sites.

MULTISORT CELL SEPARATION METHOD

BACKGROUND

The present invention is directed to a process for separation of target cells from a sample.

Cell separation methods are widespread in scientific and clinical laboratories for research, diagnostics, or clinical applications. Most of these methods are limited to small amounts of cells only. For separation of cells from a vast number of non-target cells, magnetic cell sorting or gradient density centrifugation are established technologies.

A particular challenging separation procedure is the separation of cells from whole blood, for example T cells from whole blood. To this end, erythrocytes have to be discharged before isolating or purifying the target cells. Elimination of erythrocytes can be performed, for example, by gradient density centrifugation; peripheral blood mononuclear cells (PBMC) sample preparation, erythrocyte lysis, or aggregation by, for example, multifunctional antibodies, polysaccharides, polyvinylpyrrolidone, or polyoxyethylene and subsequent centrifugation. Discharging of erythrocytes prior to isolation of target cells is for example disclosed in EP2597153A1.

After the elimination of erythrocytes or further undesired cells, subsequent process steps for isolation the target cells need to be employed. Such methods are long known in the art and use, for example, monoclonal antibodies with affinity to cell surface antigens, for example as disclosed in U.S. Pat. No. 5,840,502, U.S. Pat. No. 5,648,223, U.S. Pat. No. 5,646,004, U.S. Pat. No. 5,474,687, or U.S. Pat. No. 7,316,932.

The use of multifunctional antibodies or polymers as aggregation agents is described, for example, in WO00/73794 or U.S. Pat. No. 7,160,723. The technique disclosed comprises contacting a sample containing nucleated cells and red blood cells with an aggregation agent, removal of the aggregated red blood cells by centrifugation and further purification of the nucleated cells using antibodies recognizing the desired cells, for example, by magnetic cell sorting. These methods have the disadvantage of several process steps including a time-consuming and laborious centrifugation step.

WO 2013/076070 teaches to deplete a plurality of non-target cells by aggregation and magnetic cell sorting to obtain a suspension of cells, which are not affected by the depletion cocktail. While the cells obtained with the process are "untouched", the purity is rather low, because only a negative selection process is performed. It is not possible to obtain a specific, pure subpopulation of target cells with the process of WO 2013/076070. A similar process utilizing magnetic cells sorting is disclosed in WO01/17687A1 and WO96/31776A1.

SUMMARY

It was therefore the object of the present invention to provide a fast and simple method for removing undesired cells and separating specific target cells from biological samples like whole blood.

Surprisingly, it was found that it is possible to enrich target cells by incubating a sample in one step and subsequent magnetic separation steps without intermediate work-up by utilizing magnetic particles having different diameters.

An object of the invention is a method for enriching target cells from a sample of cells characterized by at least the steps:

a) contacting the sample with a cell aggregation agent and first magnetic particles having an iron content of 0.1 pg to 5000 pg, coupled to a first antigen recognizing moiety; and second magnetic particles having an iron content of 0.05 fg to 100 fg and coupled to a second antigen recognizing moiety to obtain mixture a)

b) applying a first magnetic field gradient to the mixture a) thereby removing the cells bound to the first antigen recognizing moiety coupled to the first magnetic particles, to obtain a mixture b) and obtaining an agglomerate comprising the cells of mixture a) bound to the cell aggregation agent c) applying a second magnetic field gradient to the mixture b) thereby immobilizing the cells bound to the second antigen recognizing moiety coupled to the second magnetic particles d) recovering the immobilized cells from the second magnetic field gradient as target cells.

In a variant of the invention, the agglomerate comprising the cells of the mixture a) bound to the cell aggregation agent and—due to the first magnetic field gradient—cells bound to the first antigen recognizing moiety coupled to the first magnetic particles are separated from mixture b).

In other words, mixture b) consists of a suspension of cells not bound to the cell aggregation agent and/or the first antigen recognizing moiety/first magnetic particles.

DETAILED DESCRIPTION

Mixture b) may be separated from the agglomerate comprising the cells of mixture a) bound to the cell aggregation agent for example by filtration, sedimentation, and/or centrifugation.

Sedimentation means gravity sedimentation at 1×g, which occurs if the container containing the sample to be processed is in an idle state, i.e., no rocking or centrifugation, allowing the aggregated cells to sediment to the bottom of the container. Centrifugation is, for example, performed at 1 to 20×g. In another embodiment, mixture a) is guided over a filter system having an appropriate mesh size. Preferably, the agglomerate is allowed to settle as sediment in the first magnetic field gradient simultaneously with the removal of the cells bound to the first antigen-recognizing moiety/the first magnetic particles and the supernatant is obtained as mixture b).

The term "antigen recognizing moiety" refers to any kind of antibody or fragmented antibody, directed against antigens expressed intracellular or extra cellular. The term relates to fully intact antibodies or fragmented antibody derivatives, e.g., Fab, Fab, F(a'b)2, sdAb, scFv, di-scFv that have been synthesized by recombinant procedures including covalent and non-covalent conjugates containing these kind of molecules.

Figure 1:
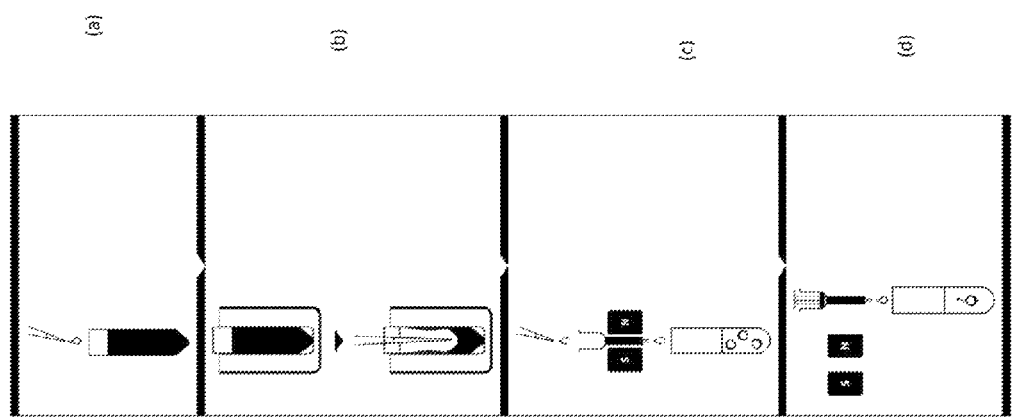
FIG. 1 shows schematically an embodiment of the method.

FIG. 1 shows schematically the method of the invention with the process steps:

(a) Incubation of the heterogeneous cell sample with i) a red blood cell aggregation agent; ii) a first type of magnetic particle (small particles), coupled to a first type of antigen-recognizing moiety; and iii) a second type of magnetic particle (large particles), coupled to a second type of antigen-recognizing moiety is shown.

(b) Exposure of mixture a to a first magnetic field gradient removes the cells bound to the first antigen-recognizing moiety coupled to the first type of magnetic particles. Simultaneously, the cells bound to the cell aggregation agent form sediment of unwanted cells. The supernatant is collected to obtain mixture b).

(c) Exposure of mixture b) by placing a MACS® Column in a MACS Separator to a second magnetic field gradient immobilizes the target cells bound to the second type of antigen-recognizing moiety coupled to the second type of magnetic particles.

(d) Recovery of the immobilized target cells from the second magnetic field gradient The present invention utilizes a magnetic field gradient generated by a magnetic source, e.g., by a permanent magnet or electromagnet. Any type and form of magnet can be used within the present invention, like the MACSxpress Separator, MACSiMAG Separator, or the QuadroMACS™ Separator commercially available by Miltenyi Biotec GmbH, Germany.

The term "magnetic particles" refers to ferromagnetic, super paramagnetic, or paramagnetic solid phases such as colloidal particles, microspheres, nanoparticles, or beads. The particles may be used in suspension or in a lyophilized state.

The magnetization of a magnetic particle is dependent on the content of iron within said particles, which is chemically present in form of iron oxides like magnetite, or maghemite. A difference in iron content by a factor of 1000 or greater allows for the separation of the first magnetic particles having high iron content by low magnetic field gradients from the second magnetic particles having low iron content which are only affected by high magnetic field gradients.

The first magnetic particles contain preferentially 0.5 pg to 500 pg, more preferentially 1 pg to 50 pg iron per particle. As first magnetic particles, MACSiBead particles may be used, which can be retained, for example, by standard magnets, like the MACSiMAG Separator (Miltenyi Biotec). As example, MACSiBeads particles, which have a diameter of a 3.5 µm contain between 3% and 10% w/w iron in dry weight.

The second magnetic particles contain preferably 0.1 fg to 50 fg, more preferentially 0.1 fg to 10 fg of iron per particle. As second magnetic particles, MicroBead particles may be used, which can be retained, for example, by standard magnets in combination with magnetic separations columns, like the QuadroMACS™ Separator in combination with LS columns obtainable from Miltenyi Biotec. The MicroBead particles of use may have a diameter of 50 to 100 nm particle containing between 30 to 60% w/w iron in dry weight.

The first and second magnetic particles used in the present invention may in addition or in alternative to the iron content be characterized by diameter. The first magnetic particles show a mean diameter of 1-5 µm, preferably 2.5-3.5 µm. In a preferred embodiment of the invention, the size of the first magnetic particles should be as monodisperse as possible, for example, with a coefficient of variation ("cv") of diameter of less than 15%, preferably less than 10%. Accordingly, the particles may be 1 µm, +/− about 0.15 µm, and preferably +/− about 0.10 µm. The second magnetic particles may have a mean diameter of 10-250 nm, preferably 30-150 nm with a cv of diameter, for example, of less than 60%, preferably less than 30%.

The term "cell sample" refers to suspensions or mixtures of cells having different phenotypes or subpopulation in different amounts, for example, cells, which are common in whole blood, peripheral blood, leukapheresis, buffy coat, umbilical cord blood, and bone marrow. Such cell samples include, for example, erythrocytes, platelets, and leukocytes, like T-cells, regulatory T-cells, B-cells, NK cells, dendritic cells, monocytes, granulocytes, and/or hematopoietic stem cells.

The term "cell aggregation agent" refers to any compound known in the art, which triggers cell aggregation for example of erythrocytes within the cell sample. For example, erythrocytes can be aggregated from whole blood and by certain reagents to form sediment in order to be able to remove the supernatant. For example, contacting whole blood with the cell aggregation agent triggers aggregate formation of erythrocytes and of some platelets, i.e., thrombocytes, resulting in the sedimentation of these undesired cell populations. The sedimentation process is further enhanced by the first magnetic particles.

The cell aggregation agents used in the present invention are preferably proteins like fibrinogen and immunoglobulin or hydroxyl-group containing polymers like dextran, hydroxyethyl starch, polyvinyl pyrrolidone (PVP), methylcellulose or hydroxypropylmethylcellulose (HPMC).

In the method according to the invention, the second magnetic field gradient may be higher than the first magnetic field gradient or the magnetic force must be increased. This can be achieved by either applying a higher second magnetic field or the use of the second magnetic particles having a higher content of magnetic material than the first magnetic particles.

By applying the first magnetic gradient, essentially all cells (i.e. 85-99%) bound to the first magnetic particles are retained on the magnet, whereas essentially all cells (i.e. 85-99%) bound to the much smaller second magnetic particles remain in mixture b).

The first and second magnetic field gradient is preferably applied by subjecting mixture b) and mixture c) on ferromagnetic separation means into the first and second magnetic field. Such ferromagnetic separation means are known in the art of magnetic cell separation and are, for example, tubes filled with magnetic materials, like particles, mesh, non-woven fibres. It is possible to adjust the second magnetic field gradient to be higher than the first magnetic field gradient by using different ferromagnetic separation means in the same magnetic field.

First and second magnetic particles are coupled to at least one antigen-recognizing moiety, which binds to at least one antigen on non-target cells and the target cells, respectively. The antigen-recognizing moieties may be mono- and/or multi-specific. Preferably, the first and/or the second magnetic particles are coupled to a plurality of different first antigen recognizing moieties. It is possible to couple the magnetic particles used in the present invention to one or more, like 2, 3, 4, 6, 8, 10, or 12 different antigen-recognizing moieties.

In one embodiment of the present invention, the cell aggregation agent is HPMC-15 and the specificity of the particles is defined by the respective antigen-recognizing moieties. The first and/or the second antigen-recognizing moiety might be selected from antibodies directed against certain cell surface markers including, e.g., CD1c, CD2, CD3, CD4, CD7, CD8, CD11b, CD14, CD15, CD16, CD19, CD23, CD25, CD27, CD34, CD36, CD38, CD43, CD45, CD45RO, CD45RA, CD56, CD61, CD123, CD127, CD133, CD193, CD235a, CD335, CD304, anti Fc_epsilon, anti T cell receptor alpha/beta, anti T cell receptor gamma/delta, anti-Biotin, anti IgE, anti HLA-DR, and combinations thereof.

As second magnetic particle for enrichment of the target cells, antibody conjugated particles, for example, with anti-CD8; anti-CD25 or anti-CD34 antibodies are used. Accordingly, in step d), cells presenting antigens for these antibodies can be recovered as target cells.

After removing the cells bound to the cell aggregation agent and the cells bound to the first antigen recognizing moiety coupled to the first magnetic particles, a mixture or cell suspension b) is obtained, which is substantially free of first particles and depleted of most cells which are not desired.

In step c), a second magnetic gradient is applied to the thus obtained mixture b). In contrast to the first magnetic gradient, the second magnetic gradient retains the cells bound to the much smaller second magnetic particles and thereby separates the target cells from the non-desired cells.

Step d) of the process of the invention is preferably carried out by removing the immobilised cells, for example, by removing the ferromagnetic separation means from the magnetic gradient and eluting the cells from the ferromagnetic separation means with buffer solution.

It is a further object of the invention to provide compositions for isolating, enriching, and/or recovering therapeutically, diagnostically, or scientifically valuable cells from a cell sample, like peripheral blood, umbilical cord blood, and/or bone marrow.

The composition according to the invention comprises a cell aggregation agent; first magnetic particles having a mean diameter of 1-5 µm, coupled to a first antigen recognizing moiety; and second magnetic particles having a mean diameter of 10-250 nm and coupled to a second antigen recognizing moiety.

The cell separation components mentioned are suited to be provided as a kit. Each kit contains the components necessary to perform the separation of desired cells from a cell-containing sample with the method described herein.

Essential components of the kit are the cell aggregation reagents and the first and second magnetic particles as mentioned herein. The particles may be available in the kit in, e.g., liquids, buffers, or in a lyophilized form and may be used for the isolation of regulatory T-cells, CD8 positive NK cells, and/or hematopoietic stem cells.

The determination of the iron content of the magnetic particles (dried material) is performed by degrading the iron oxide with acid, e.g., phosphoric acid, and quantifying the dissolved iron ions by analytical means, such as photometrical determination of colored complexes, for instance, with the Merck Spectroquant Test Kit for iron testing. Particle counts of bead suspensions can be determined by particle counters or microscopically with a Neubauer chamber. The mass concentration in the same bead suspension can be determined by transferring the bead material of a defined volume of bead suspension into water by washing, removing said water by drying and weighing the solid residue. The iron content of a particle can be calculated knowing the particle count of a bead suspension with a known mass concentration of dry bead material and the known iron content of said dried bead material. For example, MACSi-Beads with 44.5 mg per ml dry weight of beads, $1.36 \times 10^9$ particles per mg and an iron content of 4.61% w/w in the dry bead material containing 1.51 pg of iron per particle.

The particle count is not obtained directly, but estimated by calculating the weight of a single particle assuming a spherical shape and using the hydrodynamic diameter obtained by DLS measurements and the particle density of 2.5 mg/mL, according to Aaron B. Kantor, Ian Gibbons, Stefan Miltenyi, and Jürgen Schmitz in "Cell Separation Methods and Applications", Ed. Diether Recktenwald, Andreas Radbruch, Marcel Dekker, New York, 1998, p. 153-171.). For example, MicroBeads having a size of 100 nm, a dry weight of 10 mg per mL, and an iron content of 40% w/w in the dry bead material contain 0.53 fg of iron per particle.

EXAMPLES

Magnetic beads were manufactured with different process parameters resulting in different size of the particles. Particle size was characterized by Beckman Coulter Delsa Nano and Coulter Counter Z2 instruments. In the examples, first magnetic particles are referred to as "Large Magnetic particles", having a diameter of 3.5 µm and an iron content of 1.51 pg and second magnetic particles are referred to as "Small Magnetic particles" having a diameter of 0.3 µm and an iron content of 14.3 fg (if not stated otherwise). Large Magnetic particles are commercially available from Miltenyi Biotec GmbH as, for example, "anti-Biotin MACSi-Beads". Small Magnetic particles are commercially available from Miltenyi Biotec GmbH as, for example, "CD25 MicroBeads".

Example 1: Isolation of Regulatory T-Cells

Large magnetic particles were conjugated to antibodies recognizing CD8, CD14, CD15, CD19, CD123, CD127. Small magnetic particles were conjugated to antibodies recognizing CD25. Antibody bead conjugates have been titrated on human whole blood and the optimal concentration has been determined.

The magnetic bead antibody conjugates were combined including 15 mL HPMC 0.75% HPMC15 stock solution to obtain a cocktail at the previously determined amounts. The cocktail has been given to 30 mL of human whole blood, mixed, incubated for 10 minutes in a MACSmix™ Tube rotator (Miltenyi Biotec GmbH) and placed in a MACSxpress® Separator (Miltenyi Biotec GmbH) for 15 minutes. Supernatant has been further processed with MACS-Technology by using a LS-Column and QuadroMACS™ Separator (Miltenyi Biotec GmbH). Unwanted cells pass through the column. The magnetically labelled cells were flushed out by firmly pushing the plunger into the column. The isolated regulatory T-cells would be analyzed on a MACSquant Analyzer flow cytometer (Miltenyi Biotec) using a combination of fluorochrome-conjugated antibodies.

Figure 2:
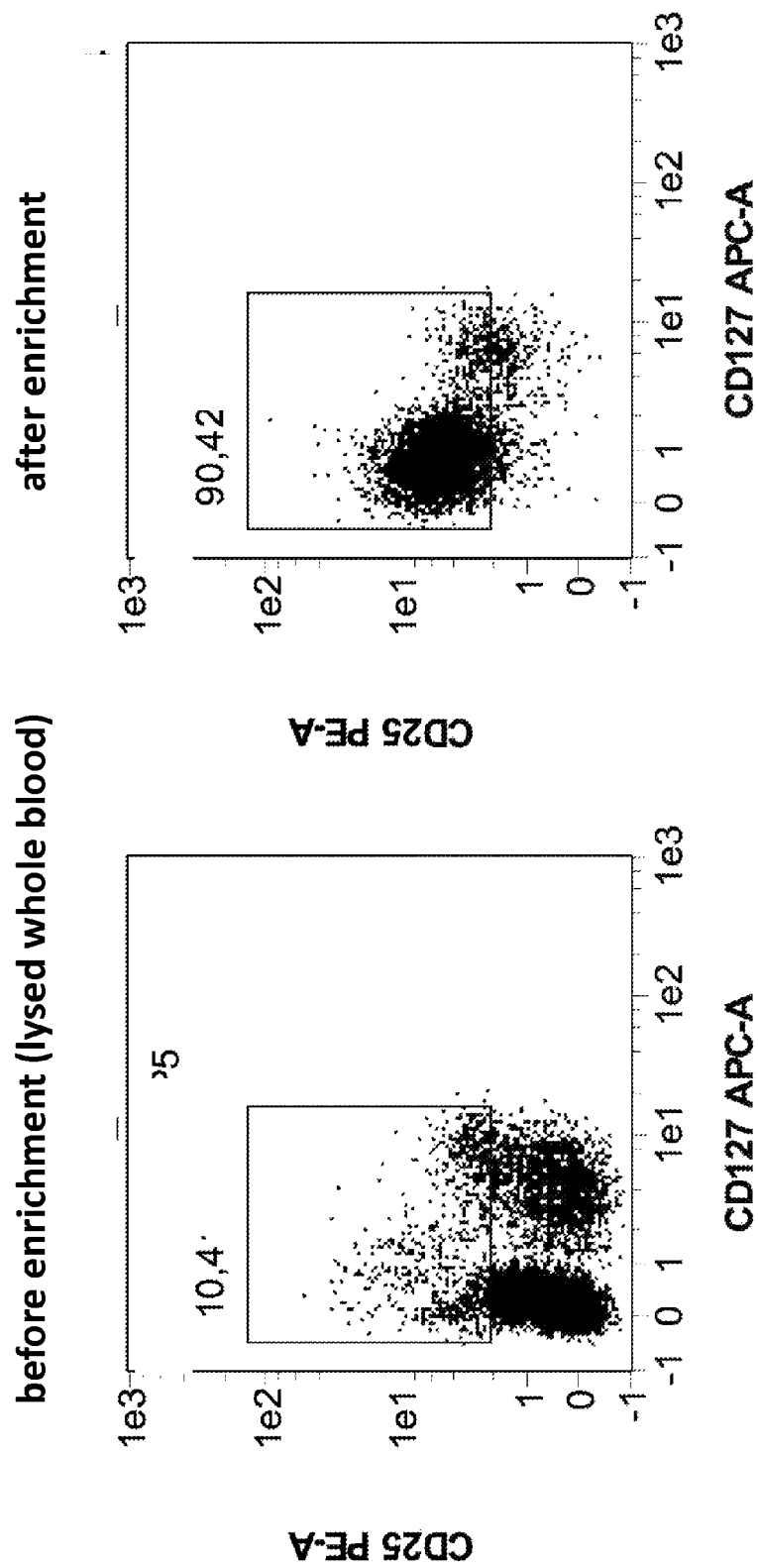
FIG. 2 shows enrichment of regulatory T-cells with the embodiment of the method.

FIG. 2 shows that according to example 1, regulatory T-cells can be enriched very quickly, within 45 min, with a purity of about 91% by using the combined labelling strategy of the invention.

Example 2: Isolation of Hematopoietic Stem Cells (HSCs)

Large Magnetic particles were conjugated to antibodies recognizing CD61 and small magnetic particles were conjugated to antibodies recognizing CD34. Antibody bead conjugates have been titrated on human whole blood and the optimal concentration has been determined.

The magnetic bead antibody conjugates were combined including 4 mL HPMC 0.75% HPMC15 stock solution to obtain a cocktail at the previously determined amounts. The cocktail has been added to 8 mL of human whole blood, mixed, incubated for 10 minutes in a MACSmix™ Tube rotator (Miltenyi Biotec GmbH) and placed in a MACSxpress® Separator (Miltenyi Biotec GmbH) for 15 minutes. Supernatant was further processed with MACS-Technology by using a LS-column and QuadroMACS™ Separator (Miltenyi Biotec GmbH) followed by a second MS-column. Unwanted cells pass through the column. The magnetically labeled cells were flushed out by firmly pushing the plunger into the column. The isolated HSCs were analyzed on a MACSquant Analyzer flow cytometer (Miltenyi Biotec) using a combination of fluorochrome-conjugated antibodies.

Figure 3:
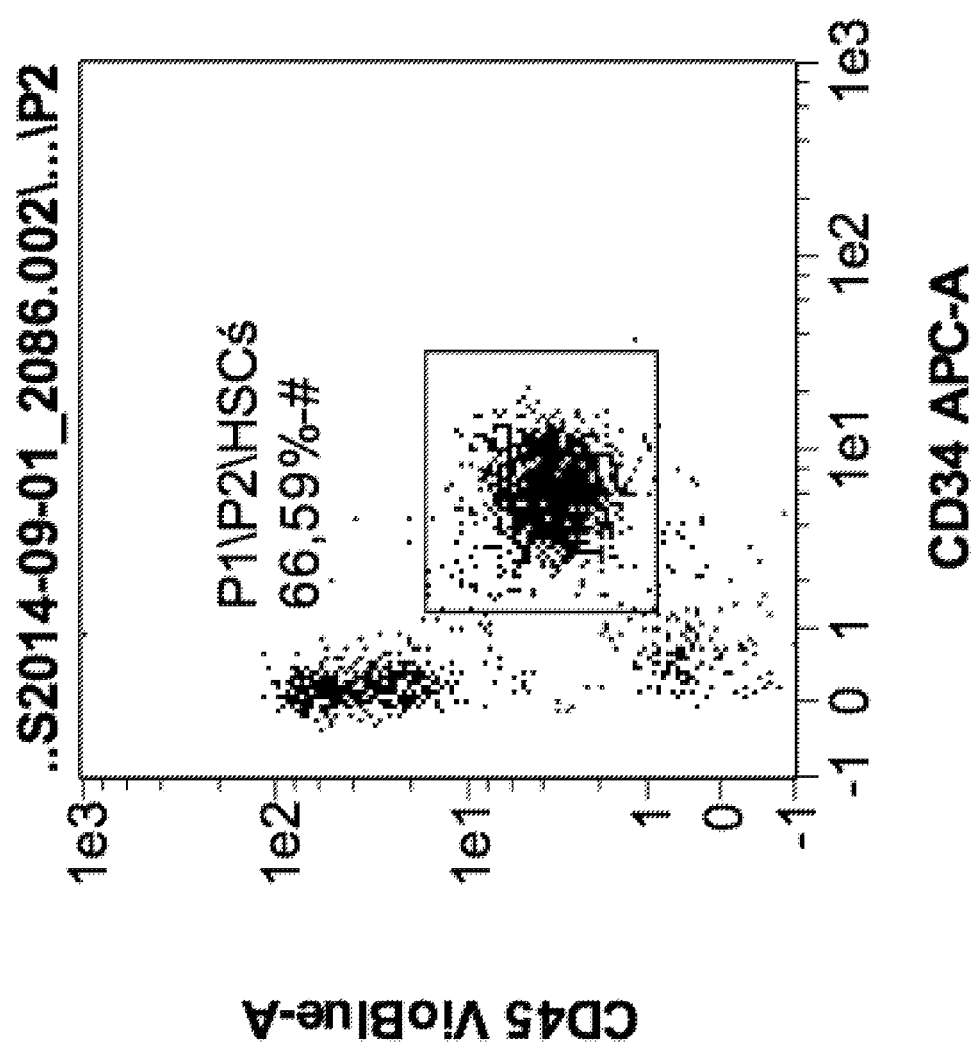
FIG. 3 shows enrichment of hematopoietic stem cells (HSCs) with the embodiment of the method.

FIG. 3 shows that according to example 2, HSCs could be enriched very quickly from whole blood, within 50 min, with a purity of about 67% by using the combined labelling strategy of the invention.

Comparative Example 1: Isolation of Regulatory T-Cells without Erythrocyte Aggregation Reagent Large magnetic particles have been conjugated to antibodies recognizing CD8, CD14, CD15, CD19 and small magnetic particles were conjugated to antibodies recognizing CD25. Antibody bead conjugates have been titrated on human whole blood and the optimal concentration has been determined.

The magnetic bead antibody conjugates have been combined with and without 4 mL HPMC 0.75% HPMC15 stock solution to obtain a cocktail at the previously determined amounts with a final volume of 4.5 mL. The cocktail has been added to 8 mL of human whole blood, mixed, incubated for 10 minutes in a MACSmix™ Tube rotator (Miltenyi Biotec GmbH) and placed in a MACSxpress® Separator (Miltenyi Biotec GmbH) for 15 minutes. Supernatant was further processed with MACS-Technology by using a LS-Column and QuadroMACS™ Separator (Miltenyi Biotec GmbH). Unwanted cells pass through the column. The magnetically labelled cells were flushed out by firmly pushing the plunger into the column. The isolated regulatory T-cells were analyzed on a MACSquant Analyzer flow cytometer (Miltenyi Biotec) using a combination of fluorochrome-conjugated antibodies.

Figure 4:
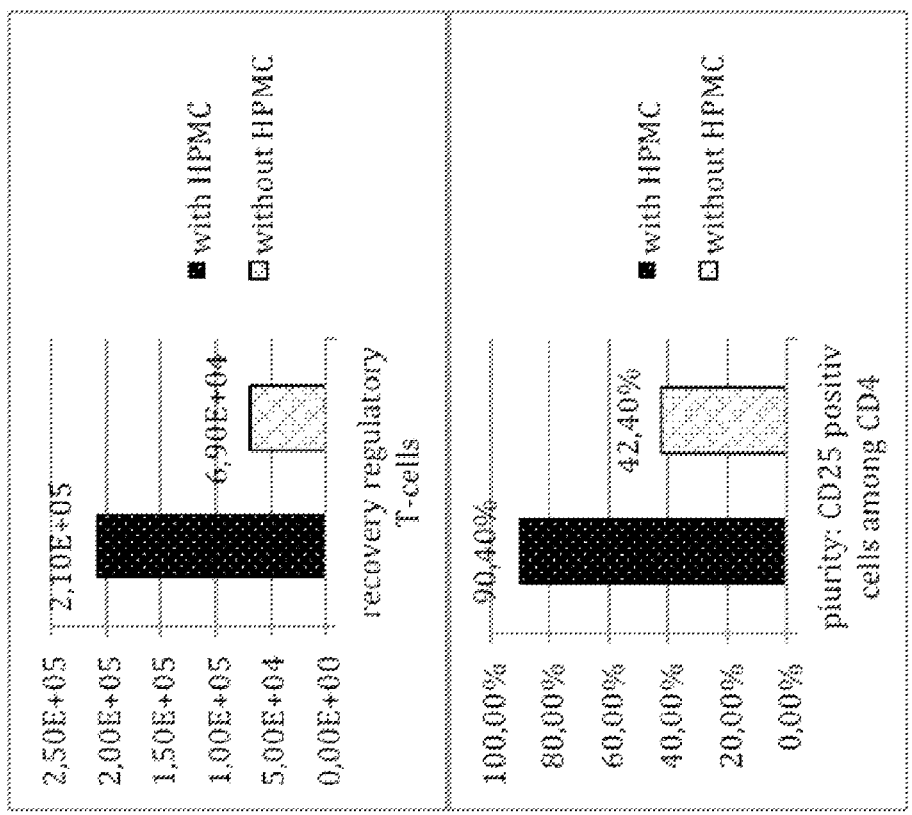
FIG. 4 shows enrichment of regulatory T-cells not according to the invention.

FIG. 4 shows that according to comparative example 1 (Without HPMC15), regulatory T-cells are obtained with purity and recovery of 42% and 6.9E+04 respectively.

Repeating comparative example 1 with HPMC15, regulatory T-cells could be achieved with a purity of 90% and recovery of 2.1E+05.

Example 3: Isolation of CD8 Positive NK Cells with Successive Magnetic Labelling Large magnetic particles, with 3 μm and 300 nm have been separated conjugated to antibodies recognizing CD3, CD4, CD14, CD15, CD19, CD36, CD61, CD123, CD193, IgE, and TCRab. Small magnetic particles were conjugated to antibodies recognizing CD8. Antibody bead conjugates have been titrated on human whole blood and the optimal concentration has been determined.

Large magnetic bead antibody conjugates were combined in a cocktail at the previously determined amounts. The cocktail was incubated with 8 mL of human whole blood in combination with 4 mL 0.75% HPMC 15 stock solution. The mixture was mixed and incubated for 10 minutes in a MACSmix™ Tube Rotator (Miltenyi Biotec GmbH) and placed in a MACSxpress® Separator (Miltenyi Biotec GmbH) for 15 minutes. Afterwards the supernatant is removed from the aggregates by pipetting into a new tube.

The small magnetic particles were added to the isolated NK cells, mixed, incubated for 10 minutes. The cells were processed with MACS-Technology by using a MS-Column and OctoMACS™ Separator (Miltenyi Biotec GmbH). Unwanted cells pass through the column. The magnetically labelled cells were flushed out by firmly pushing the plunger into the column. The isolated CD8 positive NK cells were analysed on a MACSquant Analyser flow cytometer (Miltenyi Biotec) using a combination of fluorochrome-conjugated antibodies.

Comparative Example 3

Example 3 was repeated identically except that instead of "Large magnetic particles" with 3 μm diameter, magnetic particles with 300 nm diameter were used.

In example 3, CD8 positive NK cells could be achieved with a high purity of about 93%. As shown by Comparative Example 3, by using magnetic particles with 300 nm particles instead of large magnetic particles with 3 μm diameter, the purity was reduced to 73%.

Figure 5:
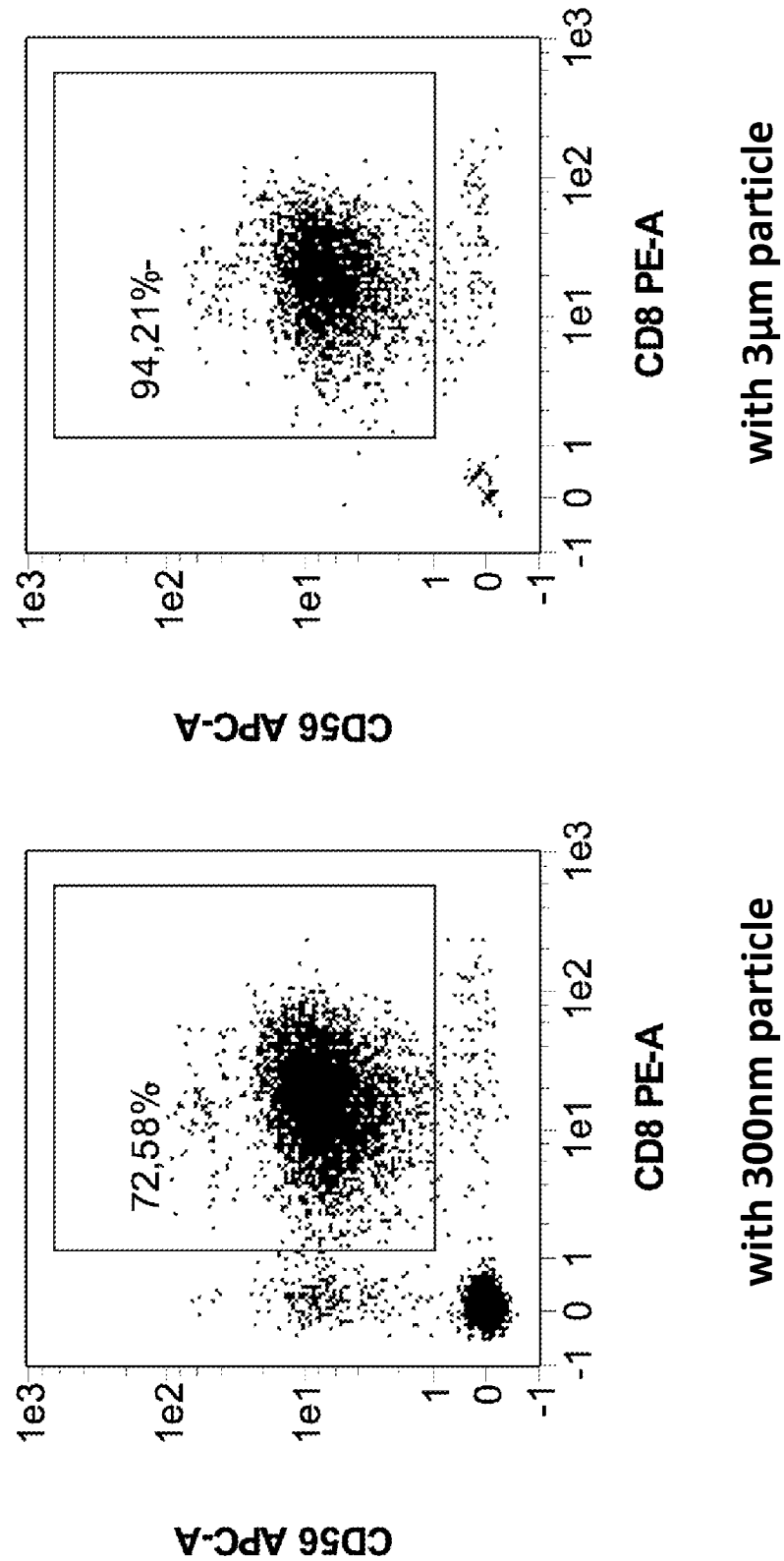
FIG. 5 shows the results of enriching CD8 positive NK cells not according to the invention.

FIG. 5 shows isolated CD8 positive NK cells direct from whole blood without any non-magnetic pre-enrichment according to Example 3 and Comparative Example 3. By using magnetic particles with a diameter of 300 nm, the positive fraction shows 27% unwanted cells due to the magnetic particles labelled to non NK-cells which were not retained during the first magnetic enrichment (FIG. 5, left side). As shown in FIG. 5, right side, by using large magnetic particles with a diameter of 3 μm labelled according to the invention, non NK-cells could remain nearly complete during the first magnetic step.

Therefore, with the method of the invention, a significant higher purity of CD8 positive NK cells after the second isolation step by using large magnetic particles with 3 μm diameter can be reached.

Example 4: Isolation of CD8 Positive NK Cells with Simultaneous Magnetic Labelling Large magnetic particles, with 3 μm have been separated conjugated to antibodies recognizing CD3, CD4, CD14, CD15, CD19, CD36, CD61, CD123, CD193, IgE, and TCRab. Small magnetic particles were conjugated to antibodies recognizing CD8. Antibody bead conjugates have been titrated on human whole blood and the optimal concentration has been determined.

Large and small magnetic bead antibody conjugates have been combined to a cocktail at the previously determined amounts. The cocktail was incubated with 4 mL of human whole blood in combination with 2 mL 0.75% HPMC 15 stock solution. The mixture was mixed and incubated for 10 minutes in a MACSmix™ Tube Rotator (Miltenyi Biotec GmbH) and placed in a MACSxpress® Separator (Miltenyi Biotec GmbH) for 15 minutes. Afterwards the supernatant was further processed with MACS-Technology by using a LS-Column and QuadroMACS™ Separator (Miltenyi Biotec GmbH). Unwanted cells pass through the column. The magnetically labelled cells were flushed out by firmly pushing the plunger into the column.

Comparative Example 4

Example 4 was repeated identically except that instead of "Large magnetic particles" with 3 μm diameter, magnetic particles with 300 nm diameter were used In example 4, CD8 positive NK cells could be achieved with a purity of about 80% by using large magnetic particles. As shown by Comparative Example 4, by using magnetic particles with 300 nm particles instead of large magnetic particles with 3 μm diameter, the purity was reduced to 6.7%

Figure 6:
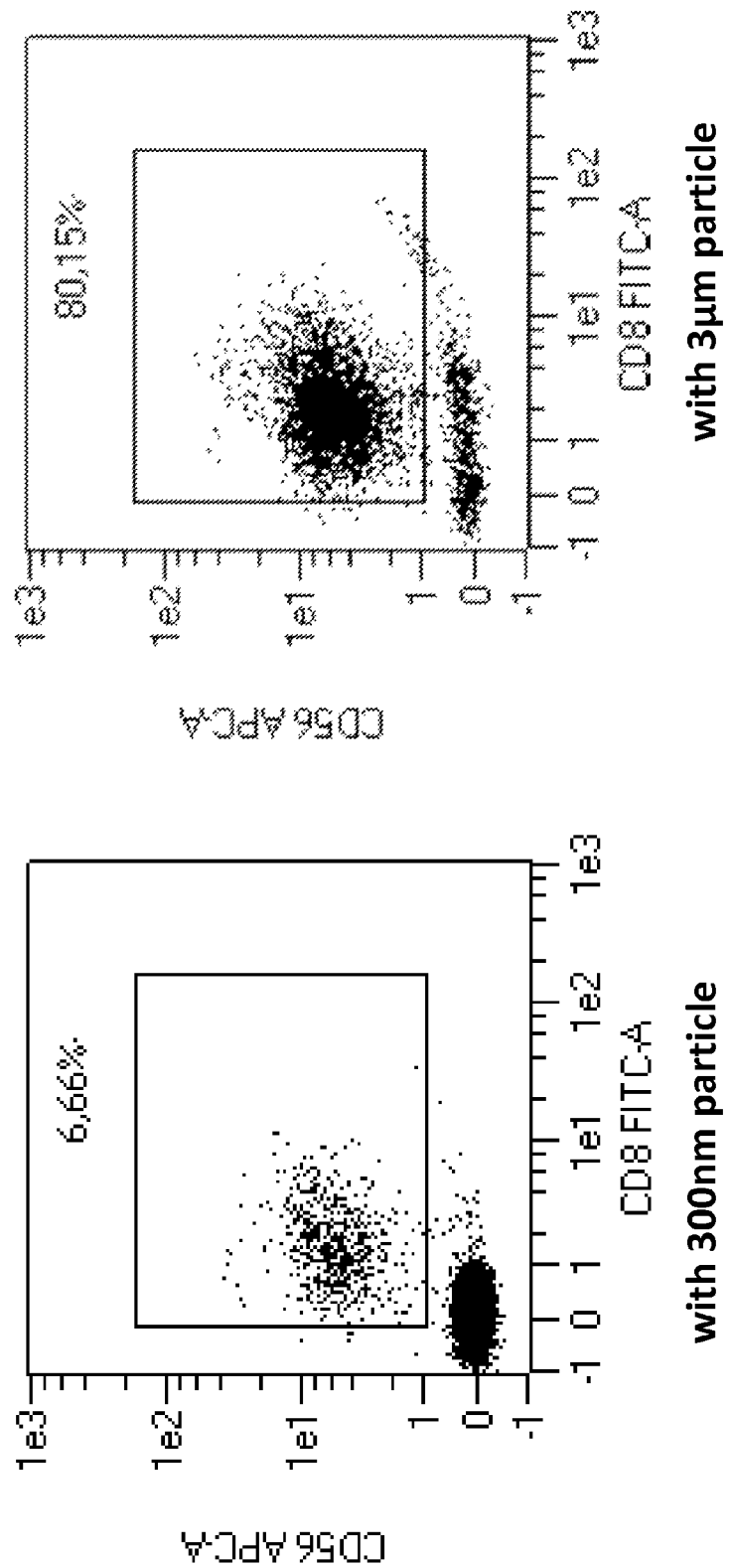
FIG. 6 shows the results of enriching CD8 positive NK cells according to the embodiment of the method.

FIG. 6 shows isolated CD8 positive NK cells direct from whole blood without any pre-enrichment according to Example 4 and Comparative Example 4. By using magnetic particles with a diameter of 300 nm instead of "large magnetic particles", the positive fraction shows 93% unwanted cells due to the magnetic particles labelled to non NK-cells which were not retained during the first magnetic enrichment (FIG. 6, left side). As shown in FIG. 6, right side, large magnetic particles with a diameter of 3 μm labelled to non NK-cells could remain nearly complete during the first magnetic step.

Therefore, with the method of the invention, an obviously higher purity of CD8 positive NK cells after the second isolation step by using large magnetic particles with 3 μm diameter can be reached.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. A method for enriching target cells from a sample of blood comprising the steps:
   a) contacting the sample with a cell aggregation agent and first magnetic particles having an iron content of 0.1 pg to 5000 pg, coupled to a first antigen recognizing moiety; and second magnetic particles having an iron content of 0.05 fg to 100 fg and coupled to a second antigen recognizing moiety to obtain mixture a);
   b) applying a first magnetic field gradient to the mixture a) thereby removing the cells bound to the first antigen recognizing moiety coupled to the first magnetic particles, to obtain a mixture b) and obtaining an agglomerate comprising the cells of mixture a) bound to the cell aggregation agent;
   c) applying a second magnetic field gradient to the mixture b) thereby immobilizing the cells bound to the second antigen recognizing moiety coupled to the second magnetic particles to obtain a mixture c); and
   d) recovering the immobilized cells from the second magnetic field gradient as target cells;
   wherein the first magnetic particles have a mean diameter of 1-5 μm and the second magnetic particles have a mean diameter of 10-250 nm.

2. The method according to claim 1, wherein the agglomerate comprising the cells of the mixture a) bound to the cell aggregation agent are separated from mixture b).

3. The method according to claim 1, wherein the second magnetic field gradient is higher than the first magnetic field gradient.

4. The method according to claim 1, wherein the first and second magnetic field gradient is applied by subjecting mixture b) and mixture c) on ferromagnetic separation means into first and second magnetic field.

5. The method according to claim 1, wherein the first magnetic particles have a coefficient of variation (cv) of diameter of less than 15%.

6. The method according to claim 1, wherein the cell aggregation reagent is selected from the group consisting of fibrinogen, immunoglobulins, dextran, hydroxyethyl starch, polyvinyl pyrrolidone (PVP), methylcellulose and hydroxypropylmethylcellulose (HPMC).

7. The method according to claim 1, wherein the first magnetic particles are coupled to a plurality of different first antigen recognizing moieties.

8. The method according to claim 1, wherein the second magnetic particles are coupled to a plurality of different second antigen recognizing moieties.

9. The method according to claim 1, wherein the first and/or second antigen recognizing moieties are antibodies against antigens selected from the group consisting of CD3, CD4, CD8, CD14, CD15, CD19, CD34, CD36, CD61, CD123, CD193, CD235a, IgE and TCRab.

10. The method according to claim 1, wherein the sample of blood is a sample of whole blood, Buffy-Coat or peripheral blood.

11. The method according to claim 1, wherein the cell aggregation agent aggregates erythrocytes.

* * * * *